US00PP32455P2

(12) United States Plant Patent
Olesen

(10) Patent No.: US PP32,455 P2
(45) Date of Patent: Nov. 17, 2020

(54) HYBRID TEA ROSE PLANT NAMED 'POULREN029'

(50) Latin Name: *Rosa hybrida*
Varietal Denomination: Poulren029

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,237

(22) Filed: Sep. 4, 2019

(51) Int. Cl.
*A01H 5/02* (2018.01)
*A01H 6/74* (2018.01)

(52) U.S. Cl.
USPC ..... Plt./136

(58) Field of Classification Search
USPC ..... Plt./137, 106, 107, 147, 148, 136
CPC ..... A01H 5/02; A01H 5/0222; A01H 5/00; A01H 6/74; A01H 6/749; C12N 9/6475
See application file for complete search history.

(56) References Cited

PUBLICATIONS

City of Belfast International Rose Trials, Trial 53 2017/2018, retrieved on Apr. 1, 2020, retrieved from the Internet at http://worldrose.org/assets/9747-rose-trials-2018-dl-(print).pdf, 2 pp. (Year: 2018).*

New Plants and Flowers, Results Rose Trial 2018 Rome, retrieved on Apr. 1, 2020, retrieved from the Internet at https://www.newplantsandflowers.com/results-rose-trial-2018-rome/, 2 pp. (Year: 2018).*

Poulsen Roser A/S retrieved on Apr. 1, 2020, retrieved from the Internet at http://www.poulsenroser.com/assortment/rose-collections/renaissance/lilo.aspx, one page. (Year: 2020).*

* cited by examiner

*Primary Examiner* — June Hwu

(57) ABSTRACT

A new garden rose plant of the Hybrid Tea class which has abundant, pink apricot flowers and attractive foliage. This new and distinct variety has shown to be uniform and stable in the resulting generations from asexual propagation.

2 Drawing Sheets

Botanical designation: *Rosa hybrida.*
Variety denomination: 'Poulren029'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2009 and the resulting seeds were planted in a controlled environment in Fredensborg, Denmark. The new variety, named 'Poulren029', originated as a single seedling from the stated cross.

The new variety may be distinguished from its male pollen parent and female seed parent primarily by the following characteristics. The male pollen parent plant has pink flowers while the new variety has pink apricot blended flowers. The female seed parent plant has white flowers while the new variety has pink apricot flowers.

The objective of the hybridization of this rose variety was to create a new and distinct variety with unique qualities, such as:

1. Uniform and abundant pink apricot flowers;
2. Vigorous, but compact growth when propagated on its own roots;
3. Exceptional disease resistance; and
4. Perfumed flowers.

This combination of qualities is not present in previously available commercial cultivars of this type, known to the inventor, and distinguish 'Poulren029' from all other varieties of which we are aware.

As part of the rose development program, Mogens N. Olesen germinated the seeds from the aforementioned hybridization during winter of 2009 and conducted evaluations on the resulting seedlings in a controlled environment in Fredensborg, Denmark. 'Poulren029' was selected in the spring of 2010 by the inventor as a single plant from the progeny of the aforementioned hybridization.

Asexual reproduction of 'Poulren029' by rooted cuttings was first done by Mogens N. Olesen in the nursery in Fredensborg, Denmark in July, 2010. This initial and other subsequent asexual propagations conducted in controlled environments have demonstrated that the characteristics of 'Poulren029' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren029'.

Specifically illustrated in FIG. 1 of the drawings are flowers at various stages of opening, petals detached, sepals detached showing reproductive flower parts, and flower buds.

Figure 1:
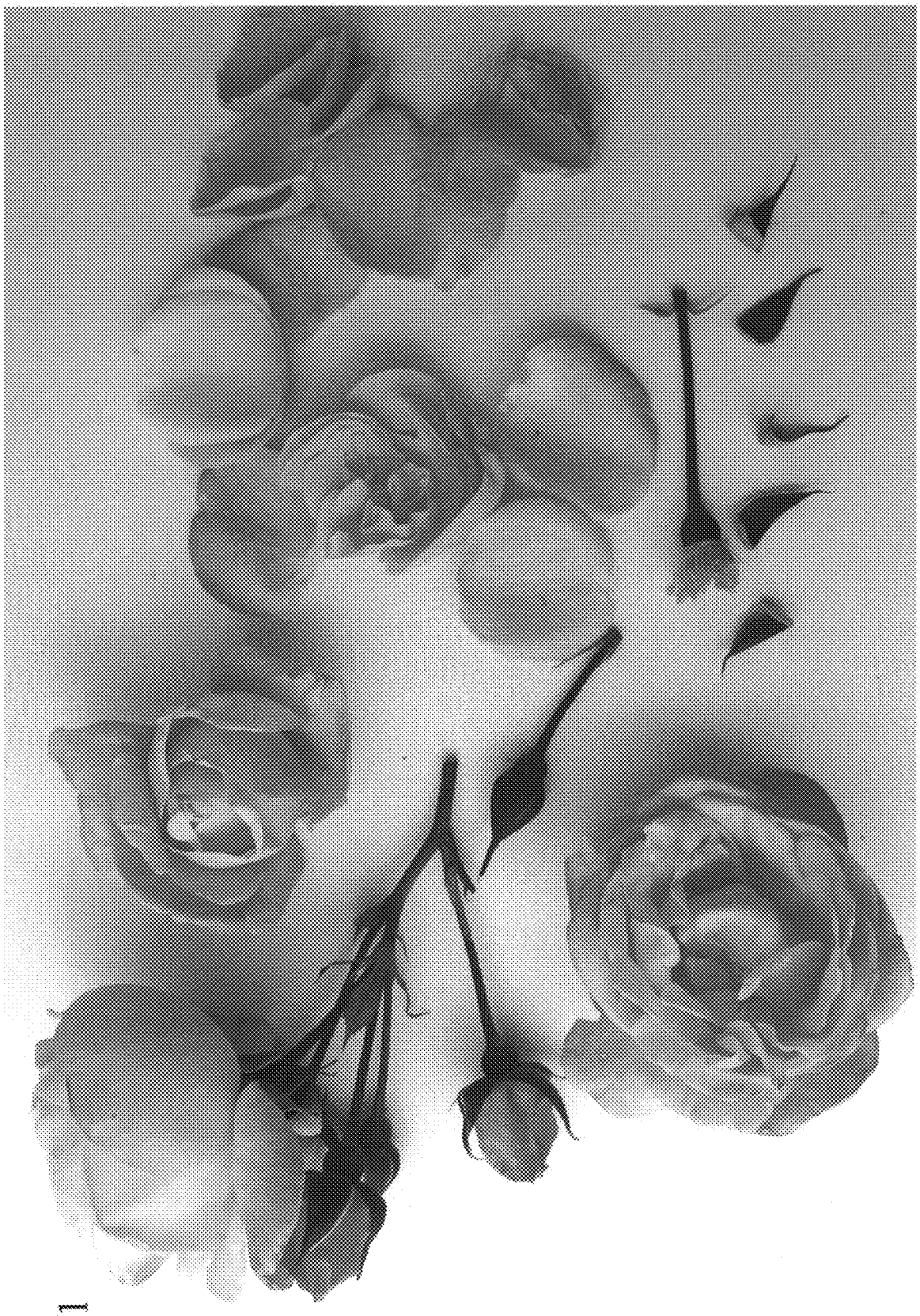
Figure 2:
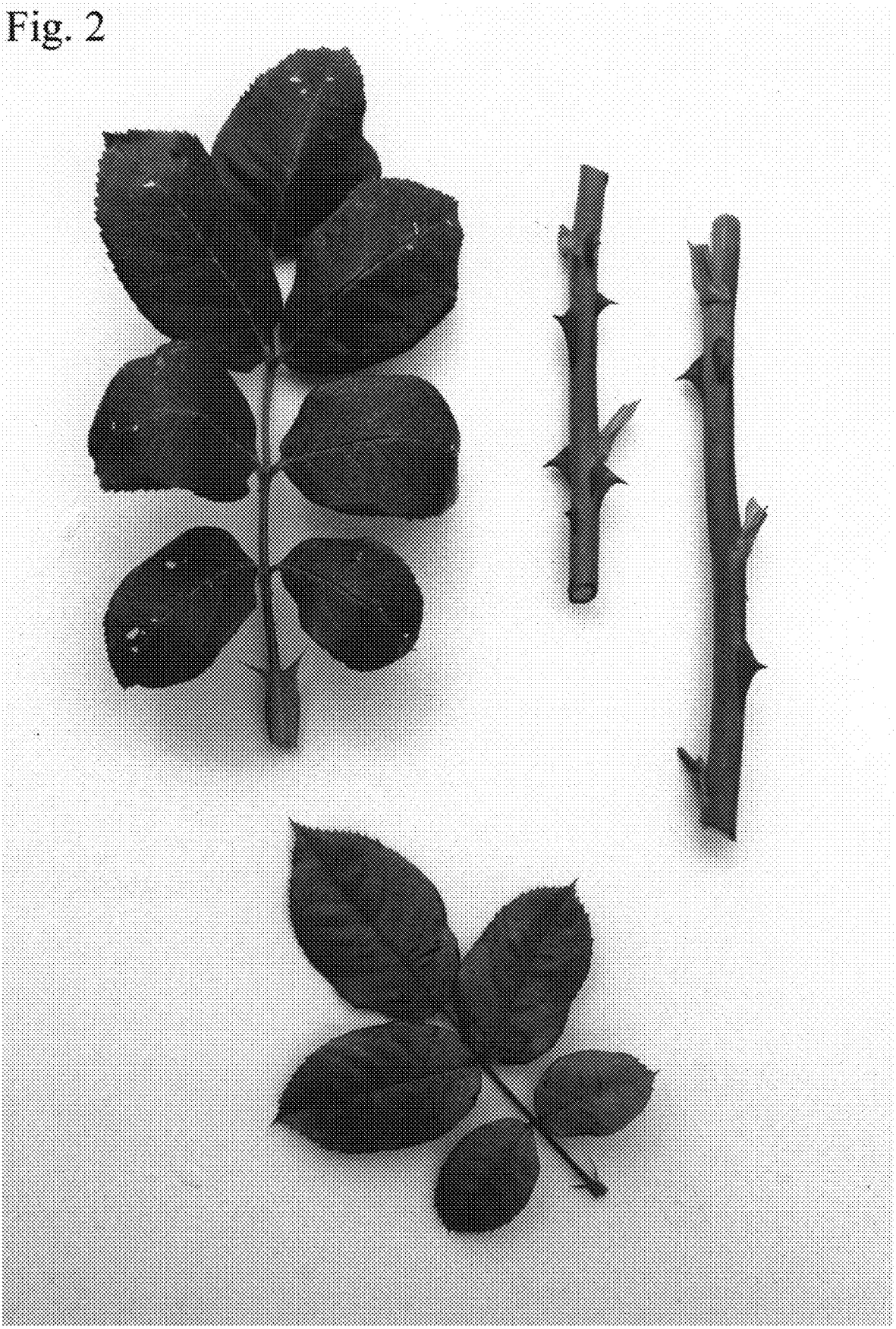

Specifically illustrated in FIG. 2 of the drawings are juvenile and mature leaves, and bare stems exhibiting thorns. Plants shown are 2 years of age.

DETAILED DESCRIPTION OF THE VARIETY

The following is a description of 'Poulren029',as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulen011', U.S. Plant Pat. No. 15,167 are compared to 'Poulren029' in Chart 1.

CHART 1

| | 'Poulren029' | 'Poulen011' |
|---|---|---|
| Petal Count | 30 petals | 80 petals |
| Flower Diameter | 90 mm | 80 to 85 mm |
| Petal Color upper surface of outer petals, upon opening | Splashed with Yellow-Orange Group 18B and Red Group 38C. Basal zone spot Yellow Group 6A | Red Group 54D |

FLOWER AND FLOWER BUD

Blooming habit: Continuous.

Flower bud:

*Size.*—Upon opening, 37 mm in length from base of receptacle to end of bud. Bud diameter is 15 mm.

*Bud form.*—Ovoid.

*Bud color.*—As sepals divide petals are Orange-Red Group N34C, with intonations of Orange Group 29A.

*Sepal inner surface.*—Color: Yellow-Green Group 145B. Surface: Lightly pubescent.

*Sepal outer surface.*—Color: Greyed-Purple Group 187B. Texture: Rough with stipitate glands.

*Sepal shape.*—Apex: Cirrhose. Base: Flat at union with receptacle.

*Sepal margin.*—Margins have weak foliaceous appendages on three of the five sepals.

*Sepal size.*—30 mm long, 11 mm wide.

*Receptacle.*—Texture: Smooth. Size: 7 mm in height, 11 mm wide. Color: Yellow-Green Group 144A with intonations of Greyed-Red Group 180A. Shape: Globular.

*Pedicel.*—Surface: Rough. Length: 50 mm. Diameter: 3 mm on average. Color: Greyed-Red Group 180A. Strength: Strong.

*Peduncle.*—Length: 3 to 6 cm. Diameter: About 5 mm. Color: Yellow-Green Group 144A with intonations of Greyed-Red Group 180B. Texture: Smooth.

Flower bud development: Flower buds are borne singly and in clusters of about 7 flower buds per stem.

Flower bloom:

*Fragrance.*—Strong perfume scent.

*Duration.*—The blooms have a duration on the plant of approximately 10 days. Petals fall cleanly away from plant after flowers have fully matured.

*Size.*—Flower diameter is 90 mm when open. Flower depth is 50 mm.

*Flower shape.*—Orbicular, high centered, double, with a high pointed center.

*Shape of flower, side view.*—The upper portion is flattened convex. The lower portion is concave.

Petalage: Under normal conditions, flowers have about 30 petals.

Petal color:

*Upon opening, outer petals.*—Upper surface: Splashed with Yellow-Orange Group 18B and Red Group 38C. Basal zone spot Yellow Group 6A. Lower surface: Orange-Red Group N34C with intonations of Red Group 37B. The basal petal spot is Yellow Group 4B.

*Upon opening, inner petals.*—Upper surface: Orange Group 24D and Red Group 38B with a small petal spot of Yellow Group 11A. Lower surface: Orange Group 29C with a small petal spot of Yellow Group 11A.

*After opening, outer petals.*—Upper surface: Red Group 56D at the middle zone, splashed with Red-Purple Group 63B. Basal zone spot Yellow Group 6A. Lower surface: Red-Purple Group 62D. The basal petal spot is Yellow Group 4B.

Petals:

*Petal reflex.*—Somewhat reflexed.

*Margin.*—Entire and uniform. Moderate undulations.

*Shape.*—Broad and elliptic. Apex shape: Rounded. Base shape: Acute.

*Size.*—45 to 60 mm (l) by 50 to 60 mm (w).

*Texture.*—Smooth.

*Thickness.*—Average.

Petaloids:

*Size.*—20 mm long by 14 mm wide.

*Quantity.*—About 5.

*Shape.*—Elliptical with an acute base and rounded apices.

*Color.*—Orange Group 24D and Red Group 38B with a petal spot of Yellow Group 11A on the upper surface. The lower surface is Orange Group 29C with a petal spot of Yellow Group 11A.

Reproductive flower parts:

*Pollen.*—None observed.

*Anthers.*—Size: 2 mm in length. Color: Greyed-Orange Group 163B. Quantity: 45 on average.

*Filaments.*—Color: Greyed-Orange Group 163B. Length: 10 mm.

*Pistils.*—Length: 5 mm. Quantity: 30 on average.

*Stigmas.*—Color: Green-White Group 157A.

*Styles.*—Color: Green-White Group 157A.

*Location of stigmas.*—Inferior in location relative to the length of the filaments and the height of the anthers.

*Hips.*—None Observed.

PLANT

Plant growth: Upright. Plants are 110 cm in height, and 95 cm wide.

Stems:

*Color of juvenile growth.*—Yellow-Green Group 144B with moderate to strong intonations of Greyed-Red Group 181A.

*Color of mature growth.*—Yellow-Green Group 144A with light intonations of Greyed-Purple Group 183B.

*Length*.—Canes are about 40 cm from the base of the plant to the flowering portion.

*Diameter*.—About 7 mm.

*Internodes*.—On mature canes about 70 mm between nodes.

*Surface texture*.—Young wood: Smooth. Older wood: Smooth.

Long prickles:

*Incidence*.—6 prickles per 10 cm of stem.

*Size*.—Average length of prickles on mature stems is 9 mm.

*Shape*.—Upper portion is linear. Lower portion is concave.

*Color*.—Juvenile prickles: Greyed-Purple Group 185A. Mature prickles: Greyed-Purple Group 185A.

Plant foliage:

*Compound leaf*.—130 to 190 mm (l)×110 (w).

*Quantity*.—2 leaves per 10 cm of stem on average.

*Leaf bearing angle to the stem*.—45 degrees.

*Color of juvenile foliage*.—Upper side: Yellow-Green Group 144A with shades of Greyed-Red Group 178B on the leaflet, and other strong intonations of Greyed-Purple Group 183A on the petiole and rachis. Lower side: Yellow-Green Group 144B shaded with intonations of Greyed-Red Group 178B.

*Color of mature foliage*.—Upper side: Yellow-Green Group 147A. Lower side: Yellow-Green Group 146B.

Plant leaves and leaflets:

*Stipules*.—Size: 17 mm long, 6 mm wide. Quantity: 2 per compound leaf. Shape: Linear, slightly broad based with outward extending apices. Margins: Finely serrated. Color:

*Petiole*.—Length: 30 mm. Diameter: 2 mm. Texture: Smooth, at the upper and lower surface. Upper surface color: Yellow-Green Group 144A. Lower surface color: Yellow-Green Group 144A.

*Rachis*.—Length: 60 mm. Texture: Upper surface is smooth. The lower surface has 2 to 3 small prickles. Upper surface color: Yellow-Green Group 144A. Lower surface color: Yellow-Green Group 144A.

*Leaflet*.—Quantity: Normally 7 leaflets. Margins: Serrated. Size: Terminal leaflets are about 60 to 65 mm long, 46 mm wide. Shape: Generally elliptical. Base: Rounded. Apex: Acute. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Hybrid Tea rose class named 'Poulren029', substantially as illustrated and described herein, due to its abundant pink apricot flowers, disease resistance, and extended period of bloom.

* * * * *